(12) United States Patent
Hickle et al.

(10) Patent No.: US 7,229,430 B2
(45) Date of Patent: Jun. 12, 2007

(54) APPARATUSES AND METHODS FOR TITRATING DRUG DELIVERY

(75) Inventors: Randall S. Hickle, Lubbock, TX (US); Jason Derouen, Lubbock, TX (US)

(73) Assignee: Scott Laboratories Inc., Lubbock, TX (US)

( * ) Notice: Subject to any disclaimer, the term of this patent is extended or adjusted under 35 U.S.C. 154(b) by 0 days.

(21) Appl. No.: 10/208,183

(22) Filed: Jul. 31, 2002

(65) Prior Publication Data

US 2003/0051737 A1 Mar. 20, 2003

Related U.S. Application Data

(60) Provisional application No. 60/308,591, filed on Jul. 31, 2001.

(51) Int. Cl.
*A61M 31/00* (2006.01)
*A61B 5/00* (2006.01)

(52) U.S. Cl. .................. 604/67; 604/504; 600/301

(58) Field of Classification Search ............ 604/890.1, 604/892.1, 65–67, 30–34, 891.1, 500, 503, 604/504, 131, 151; 705/1, 2, 3; 128/898, 128/DIG. 12, DIG. 13; 600/364, 365, 322, 600/301, 557
See application file for complete search history.

(56) References Cited

U.S. PATENT DOCUMENTS

| 4,246,894 | A | | 1/1981 | Hamacher | 128/1 R |
| 4,334,526 | A | | 6/1982 | Hamacher | 128/1 R |
| 4,741,732 | A | * | 5/1988 | Crankshaw et al. | 604/503 |
| 5,181,285 | A | | 1/1993 | Kolada | 4/657 |
| 5,820,622 | A | | 10/1998 | Gross et al. | |
| 6,053,887 | A | * | 4/2000 | Levitas et al. | 604/500 |
| 6,231,560 | B1 | * | 5/2001 | Bui et al. | 604/500 |
| 6,269,340 | B1 | | 7/2001 | Ford | 705/3 |
| 6,599,281 | B1 | * | 7/2003 | Struys et al. | 604/503 |
| 2003/0055406 | A1 | * | 3/2003 | Lebel et al. | 604/891.1 |
| 2003/0104982 | A1 | * | 6/2003 | Wittmann et al. | 514/3 |
| 2003/0145854 | A1 | * | 8/2003 | Hickle | 128/204.18 |

FOREIGN PATENT DOCUMENTS

JP 04-309362 10/1992

OTHER PUBLICATIONS

International Search Report dated May 15, 2003, for Application No. PCT/US02/24052.

\* cited by examiner

*Primary Examiner*—Matthew DeSanto
(74) *Attorney, Agent, or Firm*—Hogan & Hartson LLP

(57) ABSTRACT

A method and apparatus for reducing the workload of titrating drug to effect while leaving clinician users in control of a related procedure is described. A drug delivery device is controlled to achieve a target drug concentration at a selected site in the patient or a predetermined infusion rate waveform. The time profile of the target drug concentration or a predetermined infusion rate waveform is controlled by a drug state model that uses clinical heuristics to implement safe, pre-defined changes in the target drug concentration or infusion rate and user-commanded changes in target drug concentration or infusion rate. The invention allows time to assess the response of the patient to changes in drug level by making small incremental and conservative changes in drug level over time.

33 Claims, 11 Drawing Sheets

APPARATUSES AND METHODS FOR TITRATING DRUG DELIVERY

This application claims priority under 35 U.S.C. §119(e) to U.S. Patent Application Ser. No. 60/308,591 filed Jul. 31, 2001, which is incorporated herein in its entirety by reference.

FIELD OF THE INVENTION

This invention relates generally to apparatuses and methods for altering the drug delivery rate, time profile and/or effect site concentration to a patient in response to certain events. In particular, the invention electronically integrates, through conservative and safety-biased software that forms part of a drug state model, the titration of one or more drugs (which may be, for example, sedatives, analgesics, or amnestics) in response to electronic monitoring signals of one or more patient physiological conditions and/or user observation and input.

BACKGROUND OF THE INVENTION

Titration of a drug is commonly used by clinicians to achieve a desired effect. In general, variability in patient response to titrated drugs may be expected because an identical amount of drug may produce widely dissimilar effects in different patients. During a typical titration, therefore, clinicians may give an initial dose of a drug and observe a patient's reaction. If the desired effect is not achieved within an expected time frame (e.g., if a dose is too weak), additional increments of the drug may be administered. Each additional administration may be followed by an observation period until the desired effect is ultimately achieved. The natural variability of patient response to drugs has maintained titration as a time-honored process in the armamentarium of the clinician. The traditional titration process, however, is time-consuming and labor-intensive and may be vulnerable to human error.

When a clinician performs a painful procedure for a patient, administration and careful monitoring, or supervision of administration, of sedative and/or analgesic agents may be required. Thus, the clinician may often be physically and/or cognitively multi-tasked, thereby potentially increasing the risks of mistakes.

The traditional manual titration process may be multi-stepped and may generally be summarized as follows: (a) selecting an initial, conservative bolus dose of a given drug, based on, among others, the patient's demographic data such as age, gender, weight, height, from, among others, personal memory, a manual and drug insert, (b) delivering an initial bolus of a given drug, (c) waiting a certain time period before assessing an effect or effects of the administered drug, (d) assessing the effect or effects of the drug (possibly in the absence of equipment to objectively and consistently monitor the patient's physiological or clinical parameter(s) affected by the drug), (e) if required, selecting the size of a supplemental bolus to deliver, (f) manually delivering the supplemental bolus of given drug and (g) repeating steps (c) to (f) as required.

On the other hand, computer-controlled drug delivery systems may essentially take clinicians out of the "cognitive loop" of decision making with regard to drug administration. This "all or nothing" aspect of entirely computer-controlled drug delivery systems has hindered the acceptance of these systems by clinicians.

Rate controlled infusion (RCI) describes an infusion mode whereby clinicians define an infusion in terms of volume or mass of drug per unit time or, when normalized to patient weight, in terms of volume or mass of drug per patient weight per unit time. Generally, when using RCI, clinicians will give a loading dose infusion at a higher infusion rate to rapidly attain a desired drug level within the patient's body for a short period of time and then lower the infusion rate so that the desired drug level is maintained.

Target controlled infusion (TCI) allows clinicians to work in terms of target or effect site concentrations (ESC) instead of actual infusion rates. TCI algorithms use a pharmacokinetic (PK) model to predict target or effect site concentrations of a given drug at a given site in a patient with given demographic data such as weight, height, age and gender. Therefore, the infusion rate time profile or waveform in a TCI infusion is not constant as in RCI but generally varies with time to attain a desired target concentration.

SUMMARY OF THE INVENTION

The invention provides apparatuses and methods for providing computer-assisted titration of the level of sedative, amnestic and/or analgesic drugs in a controlled and transparent fashion that allows time for manual and/or automatic assessment of the patient's response to changing drug levels. The invention further provides computer-assisted reduction of the clinical workload without clinicians surrendering control of the administration of potent anesthetics to a computer and/or pharmacokinetic (PK) model. The invention additionally provides a means for increasing the safety of administering sedative, anesthetic or analgesic drugs to patients and enhancing the effectiveness of relieving fear and pain for patients.

The present invention provides a system which, among other things, provides a gradual change in the effect site concentration (ESC) in a patient to achieve a particular target ESC in a manner that provides a safe and effective means of changing drug levels while evaluating the patient's response to changes in drug concentration. The present invention also provides a system that allows time for an assessment of patient status as the ESC is gradually increased where, for example, in a default mode the rate of change of ESC could be deliberately slowed down over a programmable period of time.

The present invention comprises a drug delivery device that administers sedative, amnestic and/or analgesic drugs to a patient. Computer software manages the rate of drug administration and may utilize, among other things, algorithms incorporating a pharmacokinetic model. The invention includes apparatuses and methods of assessing the patient's physiological reaction and response to changing drug levels and altering, as a function of the patient's physiological reaction and response at least one from the group including, among others, the rate of change of drug level, the targeted drug level, the time profile of the infusion rate, the rate of change of ESC, the time profile of the change in ESC, the targeted ESC and the total volume to be infused over a period of time.

The invention adopts a "clinician knows best" design philosophy because the course of sedative, analgesic and/or amnestic drug action is in general both complex and influenced by many inter-related factors that may not be predictable or pre-programmable. Simultaneously, the invention automates tedious tasks, such as titrating a drug to effect, allowing clinicians to have more time to perform other tasks such as monitoring patients more closely.

The invention incorporates input from multiple sensors (both of patient and/or machine state parameters) because using the input from multiple and redundant sensors may provide a more robust system design than reliance on a single sensor. Suitable sensors can include, but are not necessarily limited to heart rate, pulse rate, respiratory rate, arterial oxygen saturation, and blood pressure monitors, and a patient responsiveness monitor. Sensors can also include monitors of machine states such as alarms status. Further, the invention implements, in general, a gradual change in target drug concentrations or infusion rate time profiles in such a way that there is time for assessment of drug effect, in objective terms and by the user, during transitions from one infusion mode, regime, profile, bolus, drug state or target to the next. The invention evaluates the responsiveness of patients (the ability of a patient to respond to a stimulus or query) directly, without requiring constant interaction and/or interpretation of a clinician. Additionally, the invention optionally alters the rate of assessment of responsiveness when infusion modes, regimes, profiles, boluses, drug states or targets are being changed or during instances when more frequent updates of responsiveness are desired such as, among others, deteriorating physiological parameters.

The invention also applies gradual titration to increase patient safety. A further objective is to "free up" clinicians' time while still leaving clinicians in charge of drug delivery and maintaining the benefits of a safe, conservative and incremental administration of potent medications.

The fields of use of the present invention include, but are not limited to, fear and/or pain management, administration of sedative, analgesic and/or amnestic drugs, anesthesia, monitored anesthesia care, deep sedation, and sedation and analgesia. Users can include clinicians, anesthesiologists, CRNAs, non-anesthesiologist physicians, nurses, technicians, and patients (self-administration). The environment of use includes all environments where sedative, analgesic or amnestic drugs are administered, (including but not limited to operating rooms, catheterization labs and hospital floors among others), patient controlled analgesia on ward floors for post-operative pain, and home use for chronic pain conditions.

DETAILED DESCRIPTION OF THE INVENTION

To accomplish a "clinician knows best" paradigm and thus allow clinician users to always remain in charge while computers perform repetitive and labor-intensive tasks, the present invention utilizes computer-assisted drug delivery as opposed to computer-controlled drug delivery. The systems and methods for computer-assisted drug delivery according to the present invention can initiate well-defined, pre-programmed actions, based on clinical heuristics, without clinician input, if the automated action (e.g., drug level reduction) will, in general, produce a safe effect. The pre-programmed actions, based on clinical heuristics, can be implemented as a transparent, finite-state algorithm wherein well-defined events (such as certain caution or warning alarms (based on the patient's physiological reaction or on the state of the drug delivery apparatus), user input, or impending loss of responsiveness to stimulation) trigger the system to transition from one drug delivery state (or "drug state") to another drug delivery state thus providing a complete drug state model. Automated actions initiated by the computer and/or software to decrease the workload of clinicians are in general limited to inherently "safe" actions, such as maintaining or decreasing drug level. In particular embodiments of the present invention, the system's controller software will, in general, not increase drug levels automatically without an explicit user (clinician, physician, nurse, etc.) or patient request for a higher drug level. The computer assisted drug delivery system of the present invention further allows users to override the pre-programmed software and automated actions, including the above-described "safe automated actions," thereby maintaining clinician control of drug delivery.

Figure 1:
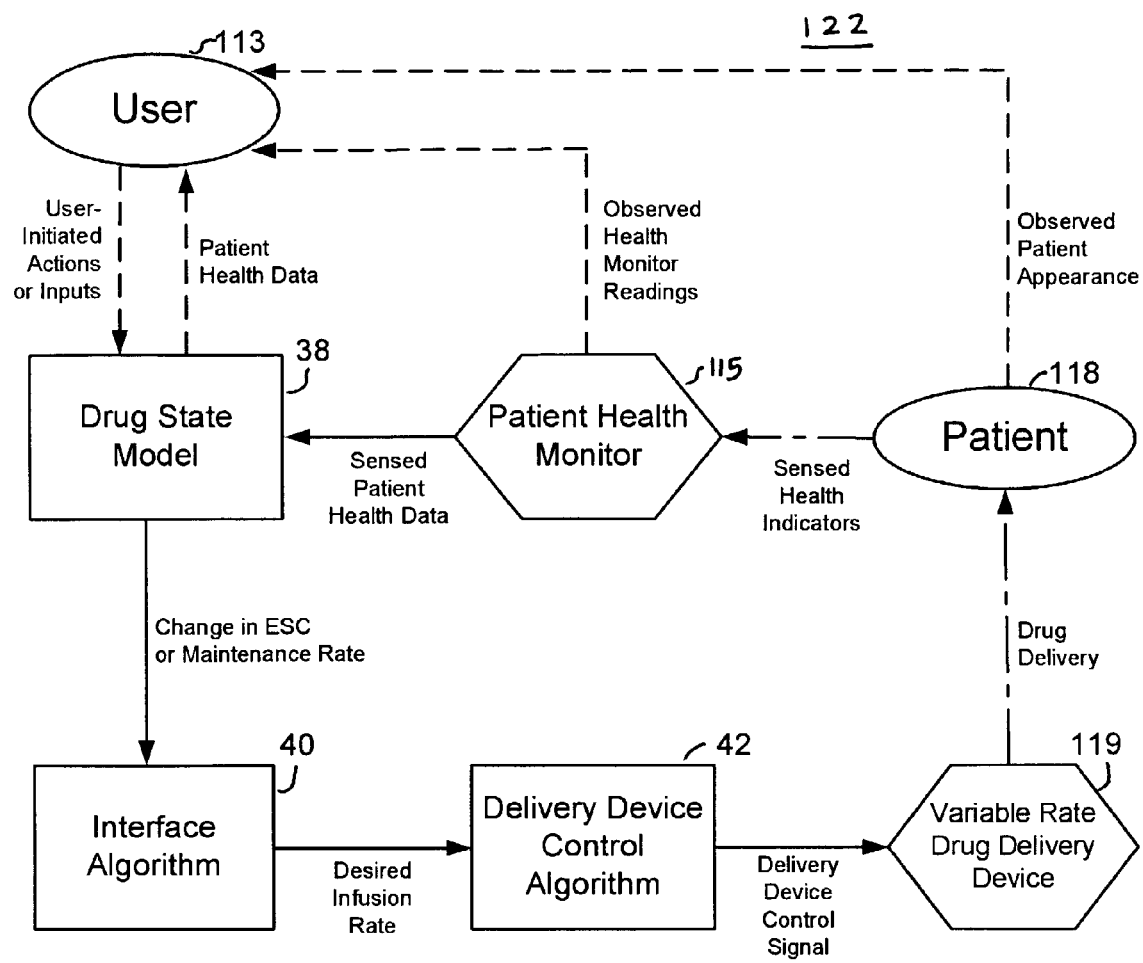
FIG. 1 is a schematic diagram depicting the interaction of a drug state model, an interface algorithm, and drug delivery control software with a patient and a user according to embodiments of the present invention.

FIG. 1 is a schematic diagram of a drug delivery system 122 showing processes used by a user 113 of a drug delivery system, and the controller of the variable rate drug delivery device 119 to manage the delivery of drugs to patient 118 according to user observation of patient appearance and data supplied by at least one patient health monitor 115 and hierarchical control algorithms 38, 40, and 42.

Figure 2:
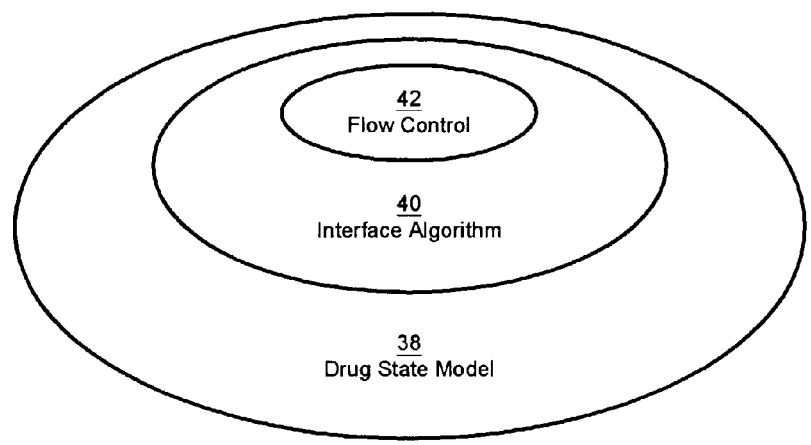
FIG. 2 is a schematic representation of a relationship between three hierarchical layers of drug administration algorithms.

FIG. 2 shows three hierarchical layers of software algorithms that a drug delivery system 122 may use to control the delivery of drugs to a patient. These layers include a Delivery Device Control or Flow Control algorithm 42 as the most basic central layer, a Drug State Model (DSM) 38 as the highest layer, and an Interface or translation algorithm 40 as an intermediate layer. The software algorithms interact with their neighboring algorithm layers so as to achieve a desired result such, as among others, a concentration of drug at an effect site compartment in the patient, i.e., an effect site concentration (ESC). The algorithms can hold the ESC as close as possible to a current value, the "current" ESC, or they can modulate the ESC towards a target value by a variable rate of change.

At the lowest level of this hierarchy, a computer manages the delivery device 122 with a flow control algorithm 42 so that the device accurately delivers a drug at a requested infusion rate. For example, the flow control algorithm, when provided with a requested infusion rate of 10 mg/kg/hr may, for example, (a) factor the size of a syringe or other drug delivery means, the drug's concentration, and the patient's weight, (b) perform particular calculations based on those factors, and (c) control the delivery mechanism so that an infusion rate as close as possible to 10 mg/kg/hr is delivered.

At the middle level of the hierarchy, an interface or translation algorithm 40 monitors certain conditions of the drug delivery process, interprets the requests from, and status of, the high level drug state model 38 layer and translates these high level, generally clinical, commands into infusion rate time profiles or waveforms that modulate over time the infusion rate requested of the flow control algorithm. This interface or translation algorithm 40 may be, among other things, a rate controlled infusion (RCI) algorithm, or a target controlled infusion (TCI) algorithm based on a pharmacokinetic model. The invention also contemplates translation layers 40 that do not use models or models running in real time but instead may use, among others, pre-programmed infusion rate templates that are adjusted via patient demographics, the total volume to be infused over a time period and drug labeling recommendations. The interface layer may also use other processes to modulate the infusion rate requested of the flow control algorithm.

An example of an RCI based algorithm uses a controller to automatically convert a user-entered loading dose and a user entered maintenance infusion rate from the units selected by the user into units for the flow control algorithm 42 to utilize. For example, a user may enter a loading dose of 5 mg of Propofol, and the translation layer 40 using RCI could automatically calculate or convert that dose into units such as cc or mg/kg, among others. The user may also enter the patient's weight via the user interface for the RCI model to calculate the loading dose in mg/kg. Similarly, the user may enter a maintenance rate of 10 mg/kg/hr, and the translation layer 40 using RCI could automatically calculate or convert that requested infusion rate into units such as mg/hr or cc/hr, among others. Once the user enters the loading dose and maintenance rate, and the translation layer 40 performs its calculation or conversion, the drug delivery system 122 may then deliver the drug accordingly so as to keep track of the total amount of infusate delivered to the patient, including that from both the initial loading dose and from the maintenance infusion.

An example of a TCI-based algorithm uses a pharmacokinetic model and a controller, preferably a proportional integral derivative ("PID") controller, for open loop, model-based control of the delivery system's pump. This PID controller may calculate a drug delivery rate error and use that error data to control the target drug levels. Based on the predictions of a pharmacokinetic model appropriately selected or modified from one or more of numerous available models, a TCI algorithm modulates the desired infusion rate requested of the delivery device in an effort to achieve a desired target concentration of a given drug at a given target or effect site within given times or time periods. A TCI software algorithm, as one embodiment of an interface or translation layer, can operate effectively on the drug delivery device computer directly or on an external computer.

According to a particular embodiment, a target-controlled infusion (TCI) algorithm comprising a controller and a pharmacokinetic model using, for example, the Schnider parameter set for propofol, may be used to control the ESC of propofol at the brain, by modulating the infusion rate of propofol. Different control algorithms can be used such as, among others, proportional (P), proportional integral (PI), and proportional integral derivative (PID) in digital or analog form, and various mathematical models such as fuzzy logic and/or neural networks. The TCI algorithm can be any suitable TCI algorithm containing an appropriate pharmacokinetic model, such as the commercially available Diprifusor® TCI module.

Figure 3:
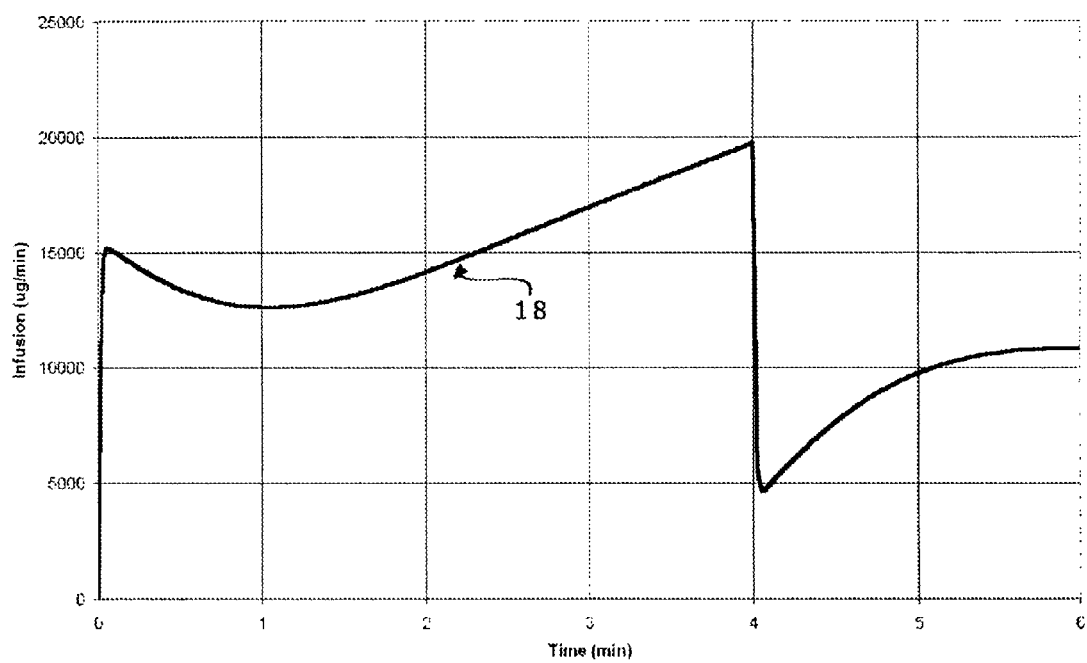
FIG. 3 is a plot of a typical rate of infusion of Propofol over time for a particular rate of increase of ESC.

FIG. 3 shows an example time plot of the actual rate of infusion of propofol for an 18 year-old, 90 kg, 140 cm tall female using an infusion pump with a 200 mg/min pumping limit set to reach a 2.0 µg/ml ESC target at a 0.5 µg/ml/min ramp-up of ESC according to one of these models. The software algorithm predicting the drug concentration at a target site and defining the rate of drug administration can employ many different pharmacokinetic models (for example, 2, 3, 4 or n compartments) now known or yet to be developed. Target and/or monitoring sites include the blood plasma, brain, central nervous system, neuromuscular junction, alveolar space, kidney, liver, pancreas, hypothalamus, heart tissue, baroreceptors and any other drug receptor laden sites or spaces in or on the body. The PK model-based software algorithm predicting the drug concentration at a target or effect site may be omitted in certain embodiments of the invention.

The interface algorithm 40 controlling the rate of change of the drug concentration can produce different time profiles of the target drug concentration at different effect sites. The time profiles can be a linear ramp from target concentration A to B or a nonlinear increase or waveform. Nonlinear drug level increases can be controlled by several variables including the starting point (target concentration A) and the initial patient response during the initiation of a drug level change.

Figure 4:
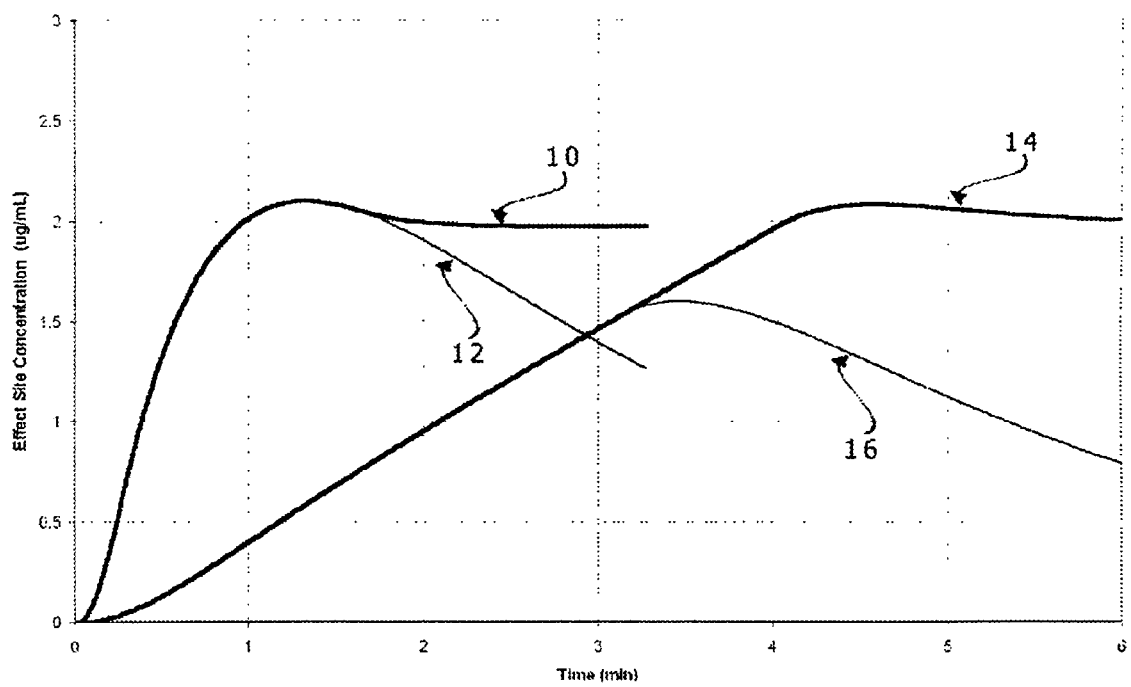
FIG. 4 is a time plot of ESC for a step input and a ramp input of ESC both with the same target and both showing respective ESC trajectories when infusion is interrupted.

FIG. 4 shows curves for the ESC over time in a patient for, by way of example, a TCI step input of 2.0 µg/ml 10 of drug as well as a TCI ramp input of 0.5 µg/ml/min 14 of drug that is targeted to reach an ESC of 2.0 µg/ml. Assuming that the patient loses consciousness when the ESC is 1.5 µg/ml and that it is immediately detected by the drug infusion system and the infusion rate is immediately set to 0, the actual ESC may overshoot the target by 0.6 µg/ml for the step input 12 compared to 0.1 µg/ml for the ramp input 16. Also, the patient may be unconscious (ESC>1.5 µg/ml) for 2.25 min for the step input 12 compared to 1 minute for the ramp input 16. In other words, the loss of consciousness may be more profound (i.e. occur at higher drug levels) and last more than twice as long with the step input compared to the ramp input. Thus, a ramp-up or other gradual means of increasing drug concentration or delivery may reduce the risk of unintended overdose or loss of consciousness. Accordingly, the drug state model 38 of the present invention utilizes a ramp-up state as a default mode for increasing drug levels to a patient.

At the highest level of the hierarchy, software representing a drug state model 38 modulates the target ESC based on certain well-defined events such as patient response, monitored physiological parameters, alarm status, and user input. The highest level layer may, in general, accept inputs that are clinical in nature, thus facilitating use by clinicians.

Figure 5:
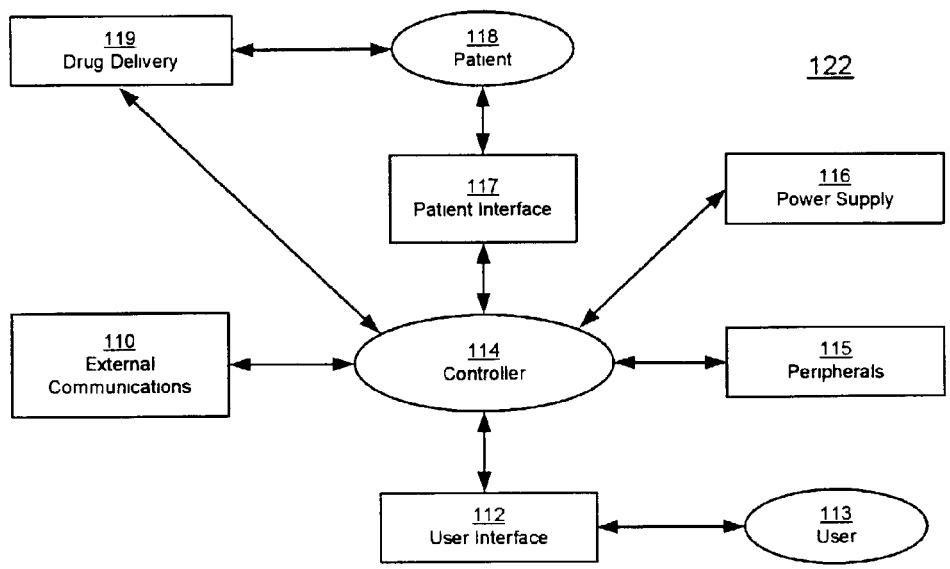
FIG. 5 is a block diagram depicting a particular embodiment of a drug delivery system for use with the drug state model of the present invention.

FIG. 5 is a block diagram depicting a particular embodiment of drug delivery system 122, in accordance with the present invention, having user interface 112, controller 114, peripherals 115, power supply 116, external communications 110, patient interface 117, and drug delivery device 119, where drug delivery system 122 is operated by user 113 in order to provide sedation and/or analgesia to patient 118. As with the interface algorithm software 40, the drug state model software 38 can operate on the controller of drug delivery device 119, on controller 114 of an integrated system comprising drug delivery device 119 or an external computer. In alternative embodiments, the invention features other hierarchical systems of control algorithms such as one with a hierarchy of only two layers where the drug state model controls the flow directly without an interface algorithm.

The drug delivery device 119 can be a syringe pump, volumetric pump, roller pump, peristaltic pump, piston pump, positive displacement pump, vane pump, gear pump, gas vaporizer and other means of controlling gas concentration or IV drug concentration. The drug administered can be a sedative, amnestic or analgesic such as propofol, remifentanil, dexmedetomidine, intravenous xenon (xenon dissolved in a lipid emulsion) and other narcotics and hypnotics. Additionally, the rate of drug infusion may be managed by computer and/or by both digital and analog circuitry. An example of such a drug delivery system 122 is disclosed and enabled by U.S. patent application Ser. No. 09/324,759, filed Jun. 3, 1999 which is herein incorporated by reference in its entirety.

The sedation and analgesia system of application Ser. No. 09/324,759 includes at least one patient health monitor device (which can be a pulse oximeter, NIBP, capnometer, EEG, EKG, and others) adapted so as to be coupled to a patient and generate a signal reflecting at least one physiological condition of the patient; a drug delivery controller supplying one or more drugs to the patient; a memory device storing a safety data set reflecting safe and undesirable parameters of at least one monitored patient physiological condition; and an electronic controller interconnected between the patient health monitor, the drug delivery controller, and the memory device storing the safety data set; wherein said electronic controller receives said signals and in response manages the application of the drugs partly in accord with the safety data set. Again, the health monitor device may include any one or more monitors for NIBP, arterial line, respiratory monitoring (among others, capnometry, transthoracic impedance plethysmography, pulse oximeter plethysmogram, the Optovent device, airway pressure, acoustical analysis), ECG assessment of heart rate, pulse oximeter assessment of heart rate and oxygen saturation and other similar tests. More than one patient-response monitor may help increase the sensitivity and specificity of the assessment and the robustness of the design.

These patient health monitor devices or patient interface 117 may generate signals reflecting physiological conditions of the patient that reflect certain warning or caution levels. These warning or caution events may be communicated to the user as alarms (e.g., caution or warning) via the user interface 112. Embodiments of user interface 112 and such alarms are disclosed and enabled by U.S. patent application Ser. No. 60/330,853, filed Nov. 1, 2001 which is herein incorporated by reference in its entirety.

A further patient monitor may be provided with the drug delivery system 122 to track a patient's responsiveness during drug delivery. An automated responsiveness test (ART) monitor may be used to provide a sensory stimulus such as, among others, an audible and/or tactile stimulus to the patient. Patients are instructed to respond to such stimuli by initiating a response means, e.g., pressing an electromechanical button, every time they receive the stimulus. The time interval between the stimuli and the patient response is called "latency" or the latent response time. In one embodiment of ART, a latency exceeding, for example, 14 seconds may be considered a "failed" ART test. A response time between, for example, 5.3 and 14 seconds may be considered a "late" response and a response time less than, for example, 5.3 s may be considered "successful". The rate at which the ART monitor queries the patient can be varied between particular settings, such as NORMAL (a query cycle every three minutes, for example), FAST (a query cycle every 15 seconds, for example), and SEARCHING (for example, a query cycle every 15 seconds until 3 consecutive response times each less than 14 seconds occur whereupon the query cycle rate is switched to NORMAL). The NORMAL setting may be a default setting and may have a user selectable delay between query cycles of, for example, 1 to 3 minutes with a default value of 3 minutes. The user may interact with the ART settings and patient response to ART information via the user interface 112 in a manner described in the application Ser. No. 60/330,853. Particular embodiments of ART in accordance with the above description and certain alternative embodiments of the features of ART are disclosed and enabled by U.S. patent application Ser. No. 60/342,773, filed Dec. 28, 2001 which is herein incorporated by reference in its entirety. The means of assessing the patient's responsiveness can alternatively include any one or more of BIS, EEG analysis, manual assessment of consciousness using different scoring systems (e.g., OAA/S—Observer's Assessment of Alertness/Sedation, Ramsay, Glasgow coma scale, etc.), or other means of consciousness or responsiveness assessment (math quiz, finger games, video games, musical note playing, etc.).

The drug state model 38 of the present invention is preferably a finite state algorithm that codifies, via clinical heuristics, safety-biased, pre-defined actions that result from, among others, patient response, monitored data, alarm conditions and user input. The drug state model according to the present invention may include a plurality of individual drug states that define heuristics for administering a drug to a patient safely under a variety of situations as well as heuristics for transitioning between the individual drug states based on certain well-defined events. These events may include, among others, a patient's ART response, Caution and Warning alarms (from patient physiological reactions to the drug administration and/or the machine states of the delivery apparatus itself), and user requests. Seven drug states and their associated heuristics are described below, though more may be implemented within the drug state model of the present invention.

These seven states include RAMP UP, RAMP DOWN, STAT UP, STAT DOWN, REDUCTION, LEVEL, and OFF. When the system initiates the "RAMP UP" drug state, it generates a gradual, linear increase in drug ESC at a predefined rate (e.g., 0.5 or 1.0 μg/ml/min) to reach a particular target ESC. When the system initiates the "RAMP DOWN" drug state, it generates a gradual linear decrease in drug ESC at a predefined rate (e.g., −0.01 or −0.3 μg/ml/min to reach a particular target ESC. The "STAT UP" drug state generates a step increase to a target ESC as fast as possible. In certain implementations, the ESC is increased rapidly while allowing no more than a certain overshoot (e.g., 15%) of the target ESC. When the system initiates the "STAT DOWN" drug state, it immediately and completely discontinues drug administration until a new target ESC is reached, for example, via an exponential decay curve which may be the most rapid possible decrease to a new target ESC. When the system initiates the "REDUCTION" drug state, it decreases the current ESC to a new target, which is some fraction (e.g., 80%) of that initial level, as fast as possible via an exponential decay. When the system initiates the "LEVEL" drug state, it maintains the current ESC as close as possible to a constant value. When the system initiates the "OFF" drug state, it immediately and completely discontinues drug administration and ESC may drop, for example, via an exponential decay curve which may be the most rapid possible decrease to zero ESC. These states of drug delivery will be explained below in more detail.

Figure 6:
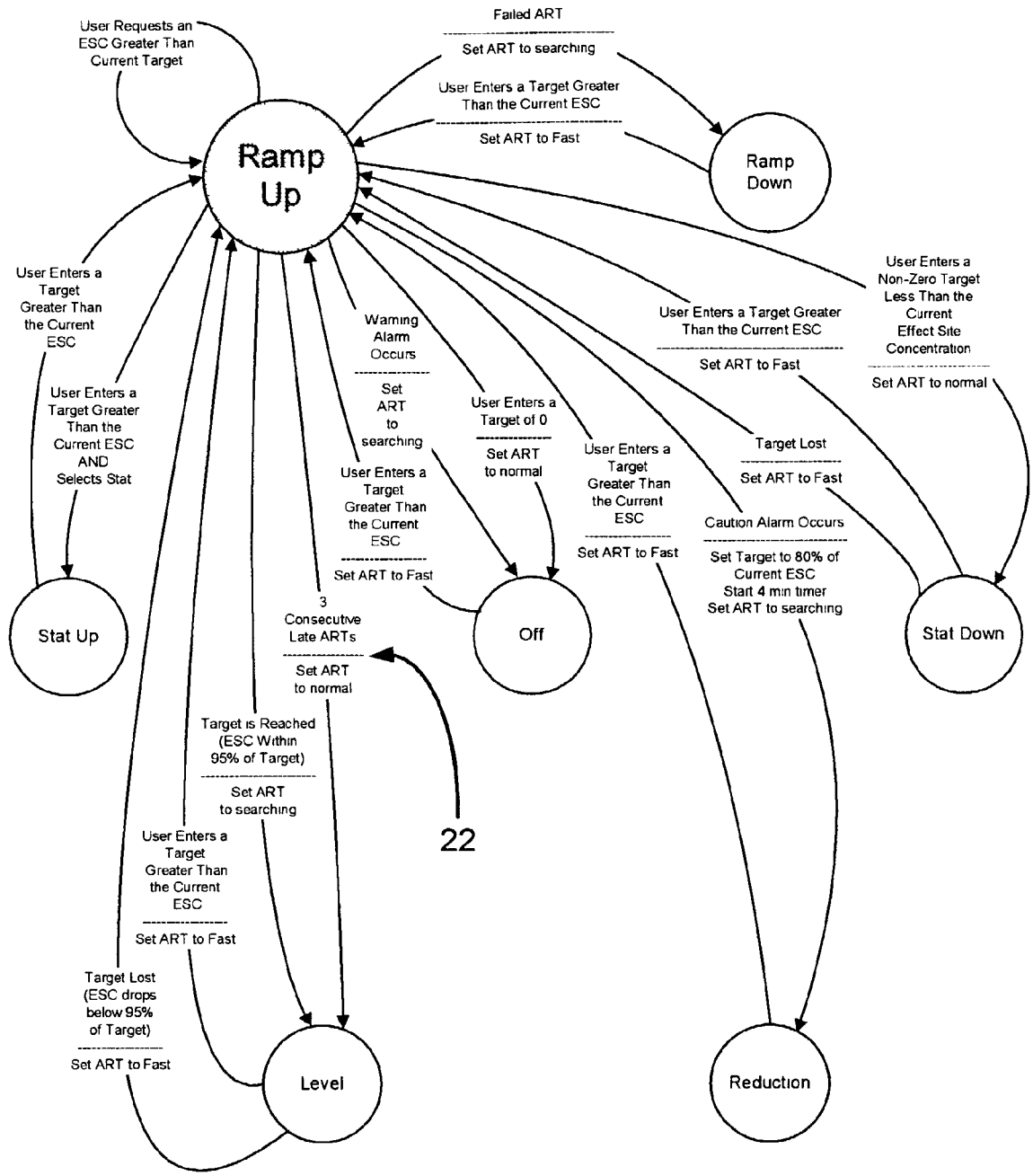
FIG. 6 shows a schematic representation of a drug state model for a RAMP UP drug state in accord with embodiments of the present invention.

FIG. 6 shows a graphical chart of the transitions to and from the RAMP UP drug state that the drug state model may initiate based on certain defined events. When the system initiates the "RAMP UP" drug state, it generates a gradual, linear increase in drug ESC at a predefined rate (e.g., 0.5 or 1.0 µg/ml/min) to reach a particular target ESC. Whenever users enter a new target ESC which is greater than the current ESC and do not select the STAT UP delivery mode, the system will enter the RAMP UP drug state. During the RAMP UP drug state, the ART query cycle frequency is set to FAST. If, while in the RAMP UP drug state, there are three consecutive "late" ART responses, the system transitions to the LEVEL drug state and sets the ART query cycle frequency to NORMAL. This transition is based on trends and/or the symptoms that the RAMP UP target ESC is higher than the ESC threshold at which the patient starts to become unresponsive. If, while in the RAMP UP drug state, the current ESC reaches a level that is within 95% of the target ESC, the system transitions to the LEVEL drug state and sets the ART query cycle frequency to SEARCHING.

Table 1a shows possible transitions away from a current drug state of RAMP UP that are possible according to the drug state model of the present invention as based on the occurrence of certain well-defined events. The transitions depicted are those from the current RAMP UP drug state to a new drug state and from the current ART query cycle frequency to a new frequency. Table 1b shows possible transitions to the RAMP UP drug state from the various other drug states and the events that would lead to those transitions according to the drug state model of the present invention.

TABLE 1a

Transitions away from RAMP UP to other drug states

| Event | New drug state | New ART frequency |
|---|---|---|
| Target reached (ESC within 95% of target) | LEVEL at target | SEARCHING |
| User enters new target: | | |
| > current ESC and selects Stat | STAT UP to new target | Unchanged |
| which is > current ESC but does not select Stat | RAMP UP to new target | Unchanged |
| which is < current ESC but > 0 | STAT DOWN to new target | NORMAL |
| which = 0 | OFF | NORMAL |
| 3 consecutive "late" ARTs | LEVEL at current ESC* | NORMAL |
| "Failed" ART | RAMP DOWN to 0 | SEARCHING |
| Caution Alarm | REDUCTION to 80% of current ESC; start 4 min. timer | SEARCHING |
| Warning Alarm | OFF | SEARCHING |

*Transition 22 (FIG. 6) of the Example run described below

TABLE 1b

Transitions leading to RAMP UP from other drug states

| Previous Drug State | Event |
|---|---|
| | User enters target which is > current ESC but does not select Stat |
| STAT UP | User enters target which is > current ESC but does not select Stat |
| RAMP UP | User enters target which is > current ESC but does not select Stat |
| LEVEL | User enters target which is > current ESC but does not select Stat |
| LEVEL | Target Lost (ESC drops below 95% of target ESC) |
| STAT DOWN | User enters target which is > current ESC but does not select Stat |
| STAT DOWN | Target Lost (ESC drops below 95% of target ESC) |
| RAMP DOWN | User enters target which is > current ESC but does not select Stat |
| REDUCTION | User enters target which is > current ESC but does not select Stat |

Figure 7:
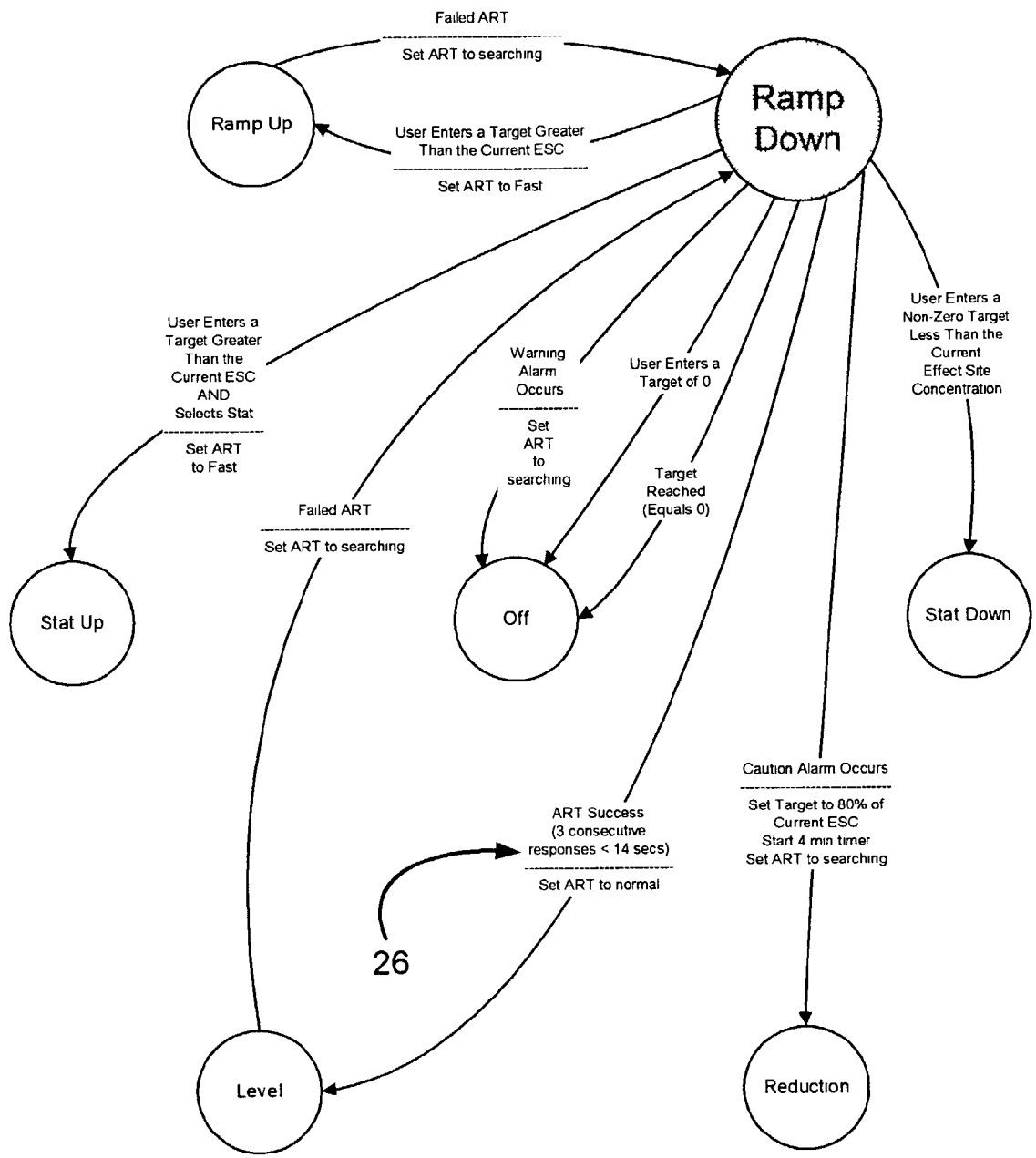
FIG. 7 shows a schematic representation of a drug state model for a RAMP DOWN drug state in accord with embodiments of the present invention.

FIG. 7 shows a graphical chart of transitions to and from the RAMP DOWN drug state that the system may initiate based on certain well-defined events. When the system initiates the "RAMP DOWN" drug state, it generates a gradual linear decrease in drug ESC at a predefined rate (e.g., −0.01 or −0.3 µg/ml/min) to reach a particular target ESC. Whenever users enter a new target ESC which is less than the current ESC and do not select the STAT DOWN delivery mode, the system will enter the RAMP DOWN drug state. If, while in the RAMP DOWN drug state, there are three consecutive "successful" ART responses, the system transitions to the LEVEL drug state and sets the ART frequency to NORMAL. If the RAMP DOWN target is zero and that target is reached during the RAMP DOWN mode, the system transitions to the OFF drug state. If a patient becomes non-responsive, as indicated by a failed ART, during either the LEVEL or RAMP UP drug states, the system may transition to the RAMP DOWN drug state with a target ESC of zero and an ART frequency set to SEARCHING such that if the patient's responsiveness returned during RAMP DOWN, as indicated by ART success, the system would transition to LEVEL at the ESC current as of when responsiveness returned.

Table 2a shows possible transitions away from a current drug state of RAMP DOWN that are possible according to the drug state model of the present invention as based on the occurrence of certain well-defined events. The transitions depicted are those from the current RAMP DOWN drug state to a new drug state and from the current ART query cycle frequency to a new frequency. Table 2b shows possible transitions to the RAMP DOWN drug state from the various other drug states and the events that would lead to those transitions according to the drug state model of the present invention.

TABLE 2a

Transitions away from RAMP DOWN to other drug states

| Event | New drug state | New ART frequency |
|---|---|---|
| Target reached (when target = 0) | OFF | unchanged |
| User enters new target: | | |
| which is > current ESC and selects Stat | STAT UP to new target | FAST |
| which is > current ESC but does not select Stat | RAMP UP to new target | FAST |

TABLE 2a-continued

Transitions away from RAMP DOWN to other drug states

| Event | New drug state | New ART frequency |
|---|---|---|
| which is < current ESC but > 0 | STAT DOWN to new target | unchanged |
| which = 0 | OFF | unchanged |
| Caution Alarm | REDUCTION of target to 80% of current ESC; start 4 min. timer | SEARCHING |
| Warning Alarm | OFF | SEARCHING |
| ART Success (3 consecutive responses < 14 s) | LEVEL at current ESC* | NORMAL |

*Transition 26 (FIG. 7) of the Example run described below

TABLE 2b

Transitions leading to RAMP DOWN from other drug states

| Previous Drug State | Event |
|---|---|
| RAMP UP | Failed ART |
| LEVEL | Failed ART |

Figure 8:
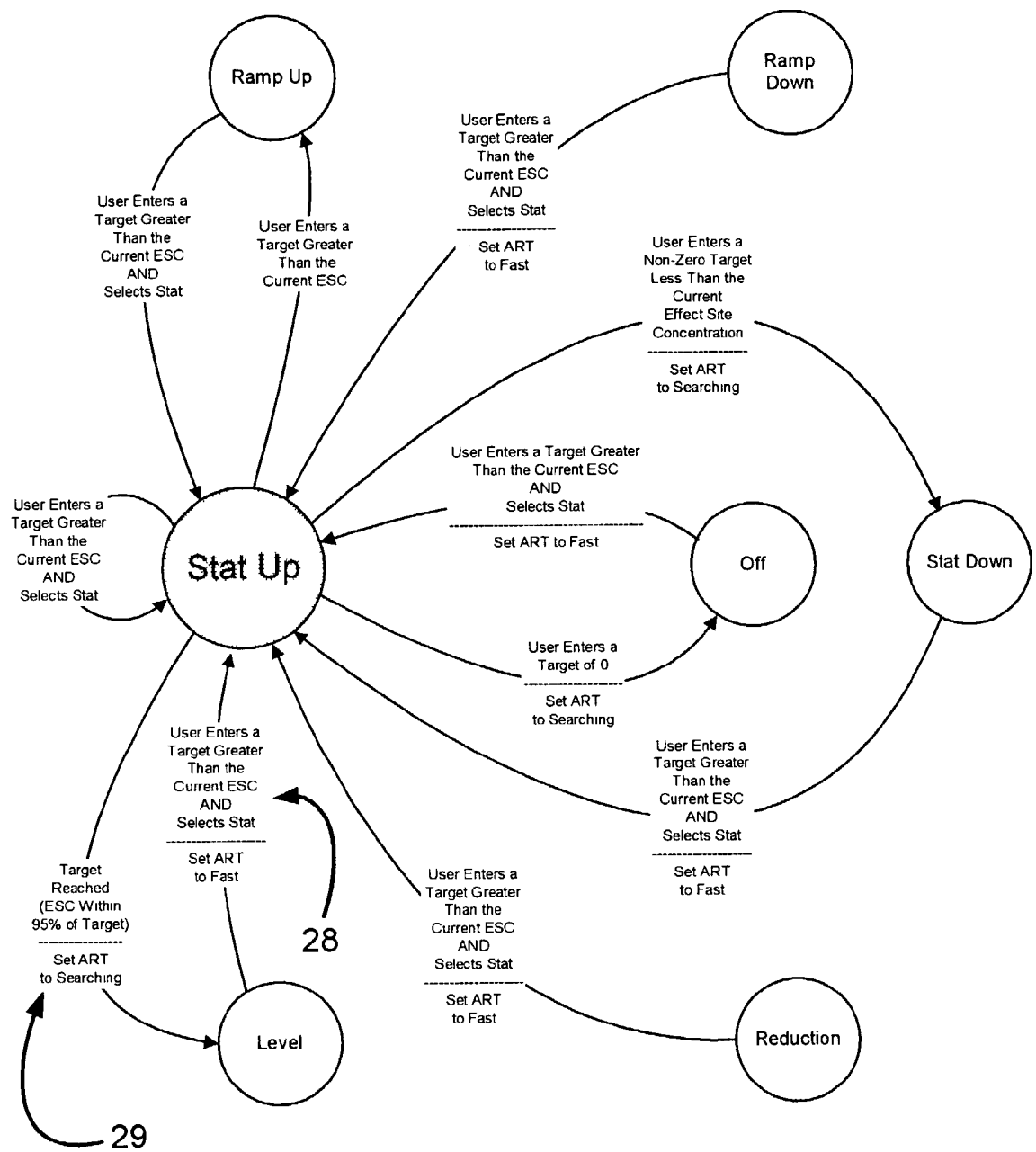
FIG. 8 shows a schematic representation of a drug state model for a STAT UP drug state in accord with embodiments of the present invention.

FIG. 8 shows a graphical chart of transitions to and from the STAT UP drug state that the system may initiate based on certain well-defined events. The "STAT UP" drug state generates a step increase to a target ESC as fast as possible. In certain implementations, the ESC is increased rapidly while allowing no more than a certain overshoot (e.g., 15%) of the target ESC. Whenever users enter a target ESC which is greater than the current ESC and select STAT delivery via the user interface, the STAT UP drug state will be initiated by the system. If the current drug state is OFF and the user enters any target ESC which is greater than 0 and chooses STAT delivery via the user interface, the STAT UP drug state will be initiated by the system to achieve that target ESC quickly. In either case, if the user does not choose the STAT delivery mode, the system will enter the RAMP UP drug state. ART query cycle frequency is set to FAST during the STAT UP drug state. If, while in the STAT UP drug state, the current ESC reaches a level that is within 95% of the STAT UP target ESC, the system transitions to the LEVEL drug state and sets the ART frequency to SEARCHING.

The invention contemplates that clinicians deliberately choose "stat up" for appropriate clinical indications which should not be over-ridden by the automated system. Therefore, in particular embodiments of the present invention, the system will not initiate a transition to the "off" drug state or set the ART frequency to "searching" upon a Warning alarm if it is in the STAT UP drug state.

Table 3a shows possible transitions away from a current drug state of STAT UP that are possible according to the drug state model of the present invention as based on the occurrence of certain well-defined events. The transitions depicted are those from the current STAT UP drug state to a new drug state and from the current ART query cycle frequency to a new frequency. Table 3b shows possible transitions to the STAT UP drug state from the various other drug states and the events that would lead to those transitions according to the drug state model of the present invention.

TABLE 3a

Transitions away from STAT UP to other drug states

| Event | New drug state | New ART frequency |
|---|---|---|
| Target reached (ESC within 95% of target) User enters new target: | LEVEL at target* | SEARCHING |
| which is > current ESC and selects Stat | STAT UP to new target | Unchanged |
| which is > current ESC but does not select Stat | RAMP UP to new target | Unchanged |
| which is < current ESC but > 0 | STAT DOWN to new target | SEARCHING |
| which = 0 | OFF | SEARCHING |

*Transition 29 (FIG. 8) of the Example run described below

TABLE 3b

Transitions leading to STAT UP from other drug states

| Previous Drug State | Event |
|---|---|
| OFF | User enters target which is > current ESC and select Stat |
| STAT UP | User enters new target which is > current ESC and select Stat |
| RAMP UP | User enters new target which is > current ESC and select Stat |
| LEVEL | User enters new target which is > current ESC and select Stat |
| STAT DOWN | User enters new target which is > current ESC and select Stat |
| RAMP DOWN | User enters new target which is > current ESC and select Stat |
| REDUCTION | User enters new target which is > current ESC and select Stat |

Figure 9:
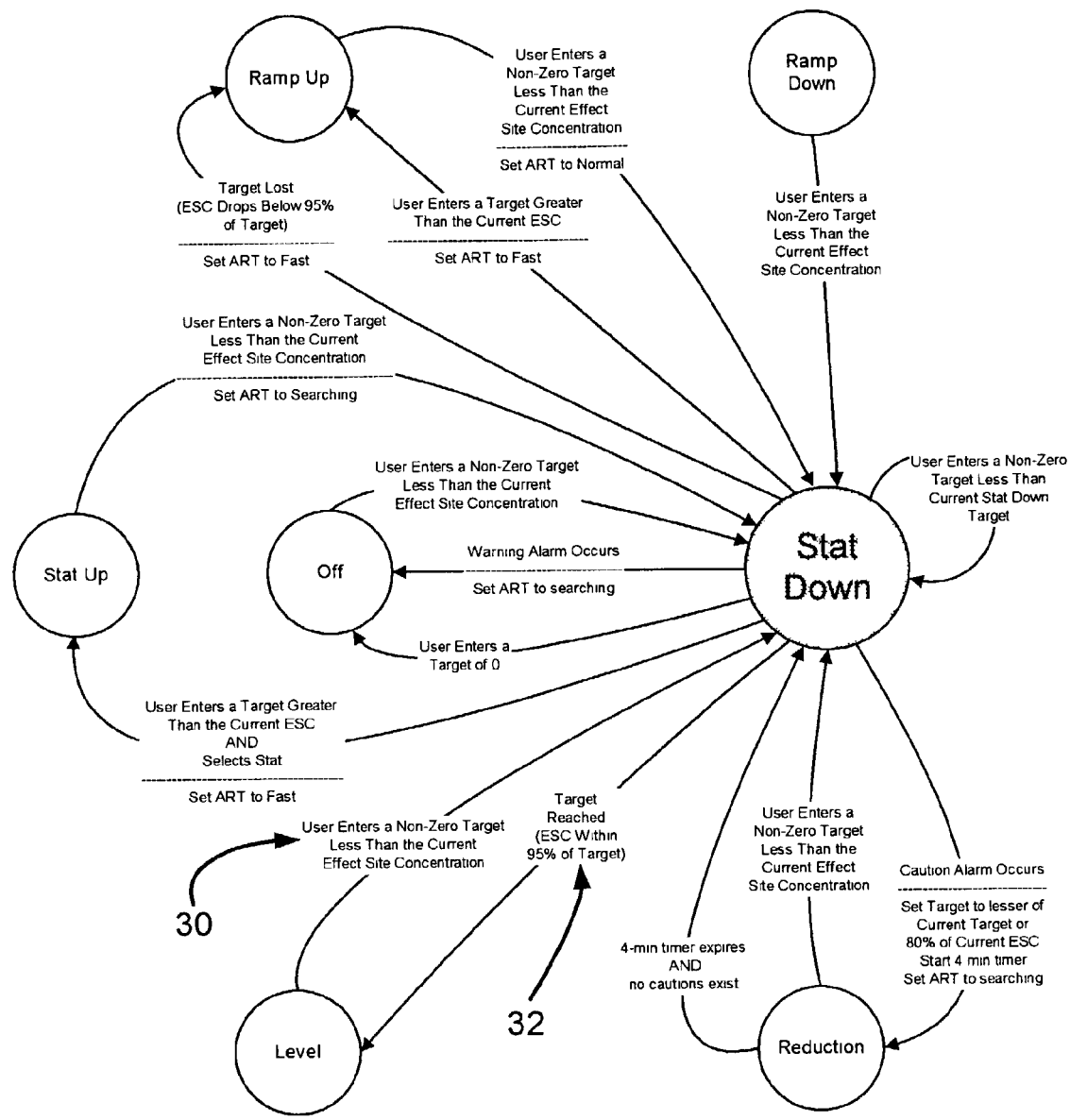
FIG. 9 shows a schematic representation of a drug state model for a STAT DOWN drug state in accord with embodiments of the present invention.

FIG. 9 shows a graphical chart of transitions to and from the STAT DOWN drug state that the system may initiate based on certain well-defined events. When the system initiates the "STAT DOWN" drug state, it immediately and completely discontinues drug administration until a new target ESC is reached, for example, via an exponential decay curve which may be the most rapid possible decrease to a new target ESC. Whenever users enter a new target ESC which is less than the current ESC and is greater than zero while in any of the other drug states, the STAT DOWN drug state may be initiated by the system. If users enter a new target ESC which is less than a current STAT DOWN target and is greater than zero, then the system may continue in the STAT DOWN drug state towards the new target ESC. If, while in the STAT DOWN drug state, the current ESC reaches a level that is within 95% of the STAT DOWN target ESC, the system transitions to the LEVEL drug state. If the ESC target is "lost" (i.e., the current ESC drops to below 95% of the target ESC; this may happen, for example, during an interruption in drug delivery to change a drug container) while in the STAT DOWN drug state, the system transitions to the RAMP UP drug state to reacquire the target ESC and the ART query cycle frequency is set to FAST.

Table 4a shows possible transitions away from a current drug state of STAT DOWN that are possible according to the drug state model of the present invention as based on the occurrence of certain well-defined events. The transitions depicted are those from the current STAT DOWN drug state to a new drug state and from the current ART query cycle frequency to a new frequency. Table 4b shows possible transitions to the STAT DOWN drug state from the various other drug states and the events that would lead to those transitions according to the drug state model of the present invention.

TABLE 4a

Transitions away from STAT DOWN to other drug states

| Event | New drug state | New ART frequency |
|---|---|---|
| Target reached (ESC within 95% of target) | LEVEL at target* | unchanged |
| User enters new target which is > current ESC and selects Stat | STAT UP to new target | FAST |
| which is > current ESC but does not select Stat | RAMP UP to new target | FAST |
| which is < current stat down target but > 0 | STAT DOWN to new target | unchanged |
| which = 0 | OFF | unchanged |
| Target lost (ESC drops below 95% of target ESC) | RAMP UP to original stat down target | FAST |
| Caution Alarm | REDUCTION of target to lesser of current stat down target or 80% of current ESC; start 4 min. timer | SEARCHING |
| Warning Alarm | OFF | SEARCHING |

*Transition 32 (FIG. 9) of the Example run described below

TABLE 4b

Transitions leading to STAT DOWN from other drug states

| Previous Drug State | Event |
|---|---|
| STAT UP | User enters new target which is < current ESC but > 0 |
| RAMP UP | User enters new target which is < current ESC but > 0 |
| LEVEL | User enters new target which is < current ESC but > 0 |
| STAT DOWN | User enters new target which is < current stat down target but > 0 |
| RAMP DOWN | User enters new target which is < current ESC but > 0 |
| REDUCTION | User enters new target which is < current ESC but > 0 |
| REDUCTION | 4 minute timer associated with a Reduction drug state expires and no cautions exist |

Figure 10:
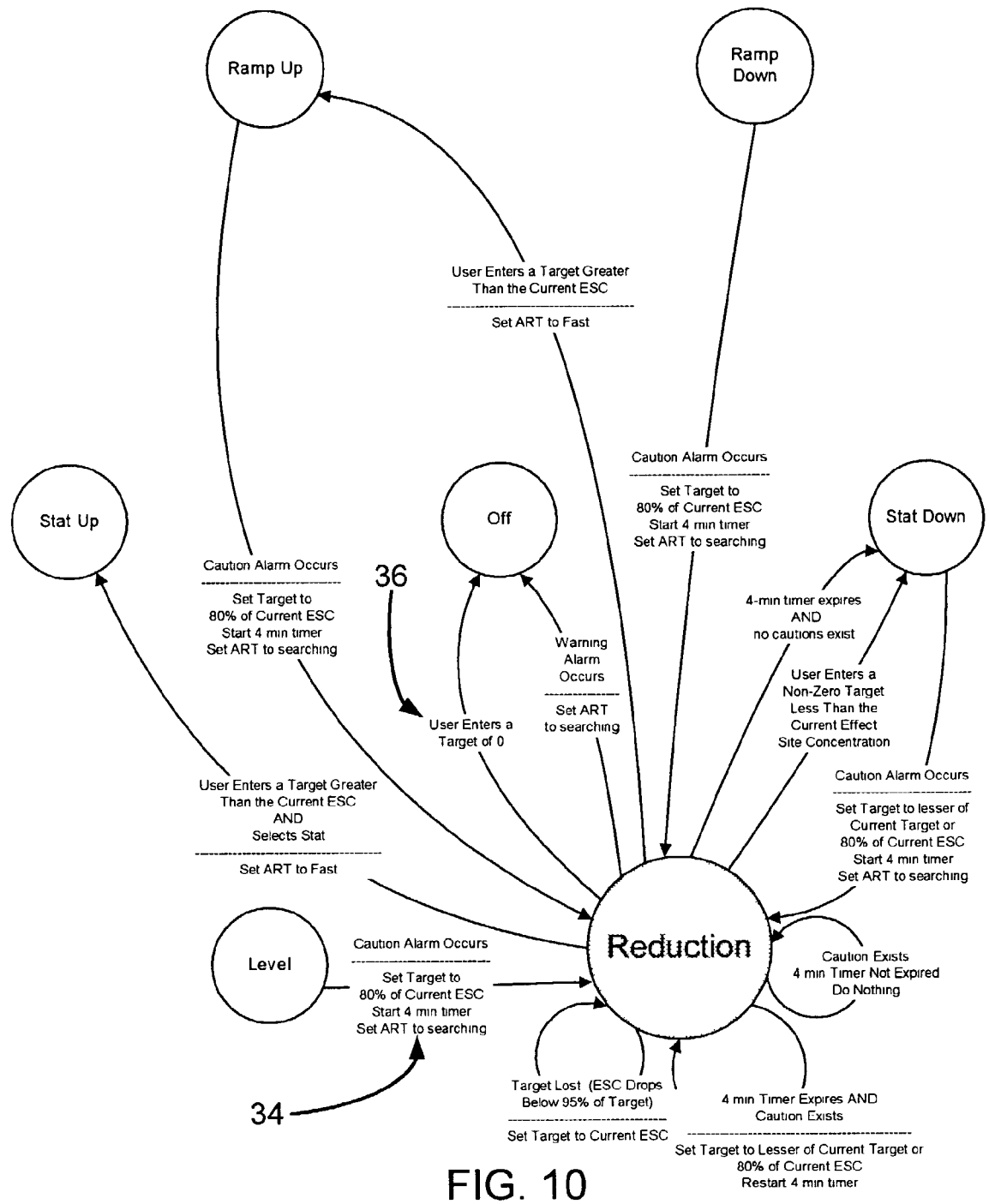
FIG. 10 shows a schematic representation of a drug state model for a REDUCTION drug state in accord with embodiments of the present invention.

FIG. 10 shows a graphical chart of transitions to and from the REDUCTION drug state that the system may initiate based on certain well-defined events. When the system initiates the "REDUCTION" drug state, it decreases the current ESC to a new target, which is some fraction (e.g., 80%) of that initial level, as fast as possible via an exponential decay. The system may accomplish this by not administering any drug to the patient until the new lower REDUCTION target ESC is reached. The system generally transitions to the REDUCTION drug state from another drug state upon a Caution alarm. ART query cycle frequency is generally set to SEARCHING upon the initiation of the REDUCTION drug state.

To prevent stacking of REDUCTION drug states due to successive Caution alarms and to allow time for drug reduction to take effect upon the initiation of the drug state, the system may start a timer upon transitioning to the REDUCTION drug state to establish a time window during which no additional drug reduction will be initiated due to a Caution alarm. The time window may be any suitable length, for example 4 minutes. Should a Warning alarm occur during the time window, the system may immediately transition to the OFF drug state regardless of the time remaining. The automatic transition to a REDUCTION drug state is consistent with the design principle that automation of drug delivery is only applied when biased towards safety. As a redundant safety measure, the system transitions from REDUCTION to STAT DOWN if the time window expires and no Caution alarms remain so as to achieve the REDUCTION target ESC in those cases that that new target had not been achieved during the time window. If at the end of the time window, no Caution alarms exist and the REDUCTION target ESC has been reached (or the current ESC is within 95% of that new target), the system will switch from REDUCTION to STAT DOWN and then immediately to LEVEL. If any Caution alarm (new or old) still exists at the end of the time window, the system sets the target ESC to the lesser of the REDUCTION target ESC or 80% of the ESC current at the expiration of the time window (i.e., a second reduction). The time window may be restarted if the target ESC is set to a second reduction level.

The system may follow the above general procedure when it transitions from the LEVEL, RAMP UP, or RAMP DOWN drug states to the REDUCTION state. When the system transitions from STAT DOWN to REDUCTION upon a Caution alarm, however, it may utilize an alternative transition procedure whereby the reduced target ESC is set to the lesser of the STAT DOWN target ESC or some fraction (e.g., 80%) of the current ESC (i.e., the ESC when the REDUCTION state is initiated). This alternative transition procedure ensures that if the target ESC set by users when selecting the STAT DOWN drug state is less than that fraction of the ESC prevailing upon the transition to REDUCTION, then the automated reduction will not override the judgment of the user. This is consistent with the "clinician knows best" philosophy. If the ESC target is "lost" (i.e., the current ESC drops to below 95% of the target ESC; this may happen, for example, during an interruption in drug delivery to change a drug container) while in the REDUCTION drug state, the system resets the target ESC to the current ESC.

Preferably, the system does not automatically transition from STAT UP to REDUCTION upon a Caution alarm. This is also consistent with the "clinician knows best" design philosophy and the deliberate goal to trust and empower clinicians. The invention contemplates that clinicians deliberately choose "stat up" for appropriate clinical indications which should not be over-ridden by the automated system.

Table 5a shows possible transitions away from a current drug state of REDUCTION that are possible according to the drug state model of the present invention as based on the occurrence of certain well-defined events. The transitions depicted are those from the current REDUCTION drug state to a new drug state and from the current ART query cycle frequency to a new frequency. Table 5b shows possible transitions to the REDUCTION drug state from the various other drug states and the events that would lead to those transitions according to the drug state model of the present invention.

TABLE 5a

Transitions away from REDUCTION to other drug states

| Event | New drug state | New ART frequency |
|---|---|---|
| User enters new target: | | |
| which is > current ESC and selects Stat | STAT UP to new target | FAST |
| which is > current ESC but does not select Stat | RAMP UP to new target | FAST |
| which is < current ESC but > 0 | STAT DOWN to new target | unchanged |
| which = 0 | OFF* | unchanged |
| Target lost (ESC drops below 95% of target) | REDUCTION of target to current ESC | unchanged |
| When Reduction starts with 4 minute timer and: | | |
| 4 minute timer expires and no cautions exist | STAT DOWN | unchanged |
| 4 minute timer expires and cautions do exist | REDUCTION of target to lesser of current target of 80% of current ESC; restart 4 minute timer | unchanged |
| 4 minute timer has not yet expired but cautions exist | Do nothing | unchanged |
| Warning Alarm | OFF | SEARCHING |

*Transition 36 (FIG. 10) of the Example run described below

TABLE 5b

Transitions leading to REDUCTION from other drug states

| Previous Drug State | Event |
|---|---|
| RAMP UP | Caution Alarm |
| LEVEL | Caution Alarm |
| STAT DOWN | Caution Alarm |
| RAMP DOWN | Caution Alarm |
| REDUCTION | Target lost (ESC drops below 95% of target) |
| REDUCTION | When Reduction starts with 4 minute timer that expires and cautions exist |

Figure 11:
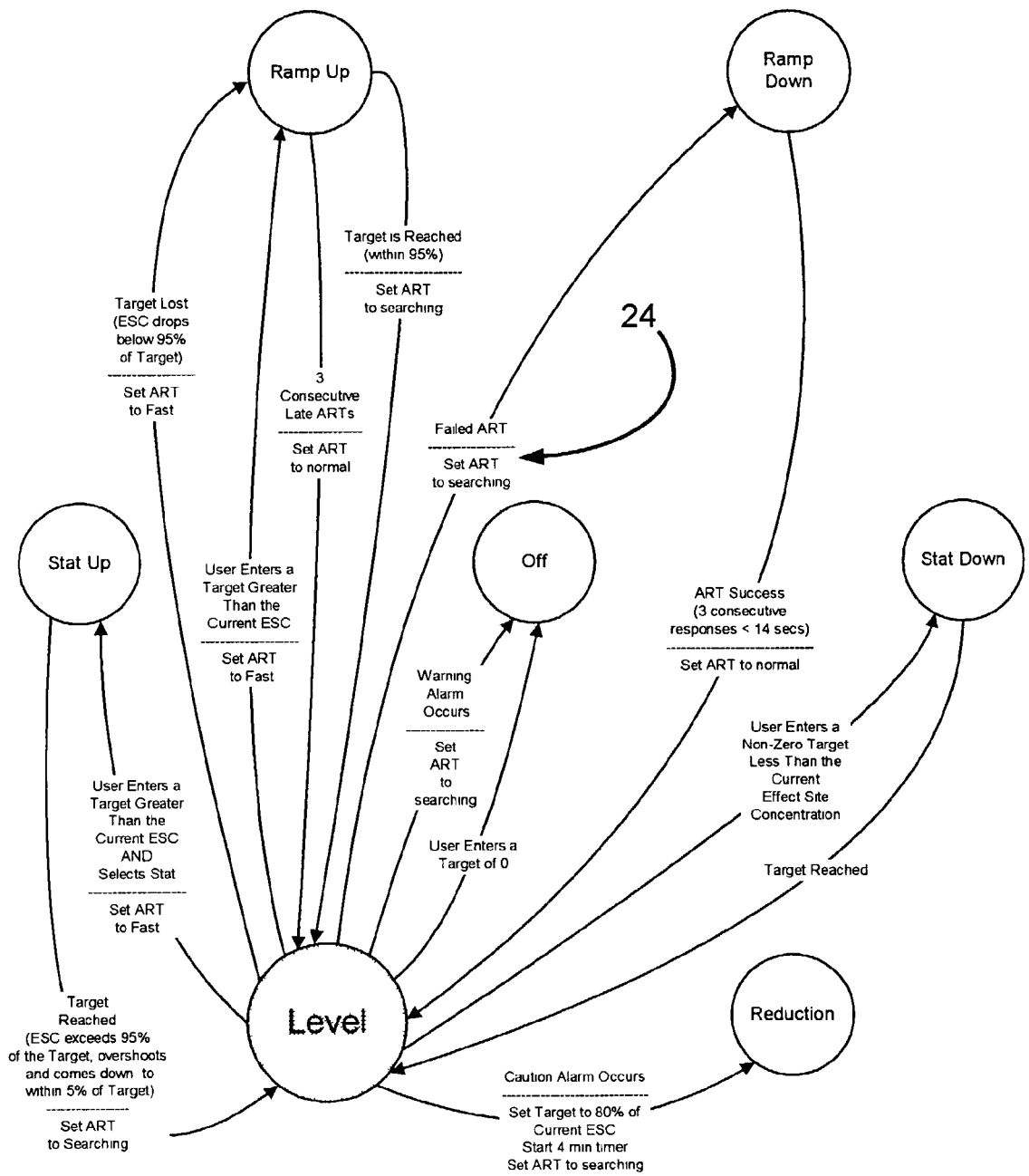
FIG. 11 shows a schematic representation of a drug state model for a LEVEL drug state in accord with embodiments of the present invention.

FIG. 11 shows a graphical chart of transitions to and from the LEVEL drug state that the system may initiate based on certain well-defined events. When the system initiates the "LEVEL" drug state, it maintains the current ESC as close as possible to a constant value. The system may transition from another drug state to LEVEL whenever a target ESC is reached. A target ESC may be considered to have been reached by the system whenever the current ESC is within 95%, or some other value, of the target ESC. ART query cycle frequency may be set to SEARCHING when the system transitions from another drug state to LEVEL based on a target ESC being reached and to NORMAL when the system transitions to LEVEL based on a "late" ART (i.e., three consecutive late responses) during RAMP UP or on a "successful" ART during RAMP DOWN. If the ESC target is "lost" (i.e., the current ESC drops to below 95% of the target ESC; this may happen, for example, during an interruption in drug delivery to change a drug container) while in the LEVEL drug state, the system transitions to the RAMP UP drug state to reacquire the target ESC and the ART query cycle frequency is set to FAST.

Table 6a shows possible transitions away from a current drug state of LEVEL that are possible according to the drug state model of the present invention as based on the occurrence of certain well-defined events. The transitions depicted are those from the current LEVEL drug state to a new drug state and from the current ART query cycle frequency to a new frequency. Table 6b shows possible transitions to the LEVEL drug state from the various other drug states and the events that would lead to those transitions according to the drug state model of the present invention.

TABLE 6a

Transitions away from LEVEL to other drug states

| Event | New drug state | New ART frequency |
|---|---|---|
| User enters new target: | | |
| which is > current ESC and selects Stat | STAT UP to new target* | FAST |
| which is > current ESC but does not select Stat | RAMP UP to new target | FAST |
| which is < current ESC but > 0 | STAT DOWN to new target** | unchanged |
| which = 0 | OFF | unchanged |
| Target lost (ESC drops below 95% of target ESC) | RAMP UP to original target | FAST |
| Failed ART | RAMP DOWN to 0*** | SEARCHING |
| Caution Alarm | REDUCTION to (80% of current ESC; start 4 min. timer**** | SEARCHING |
| Warning Alarm | OFF | SEARCHING |

*Transition 28 (FIG. 11) of the Example run described below
**Transition 30 (FIG. 11) of the Example run described below
***Transition 24 (FIG. 11) of the Example run described below
****Transition 34 (FIG. 11) of the Example run described below

TABLE 6b

Transitions leading to LEVEL from other drug states

| Previous Drug State | Event |
|---|---|
| STAT UP | Target Reached (when current ESC is within 95% of target; current ESC may overshoot target before coming down to within 95% of target) |
| RAMP UP | 3 Consecutive "late" ARTs |
| RAMP UP | Target Reached (when current ESC is within 95% of target) |
| RAMP DOWN | ART "success" |
| STAT DOWN | Target Reached (when current ESC is within 95% of target) |

Figure 13:
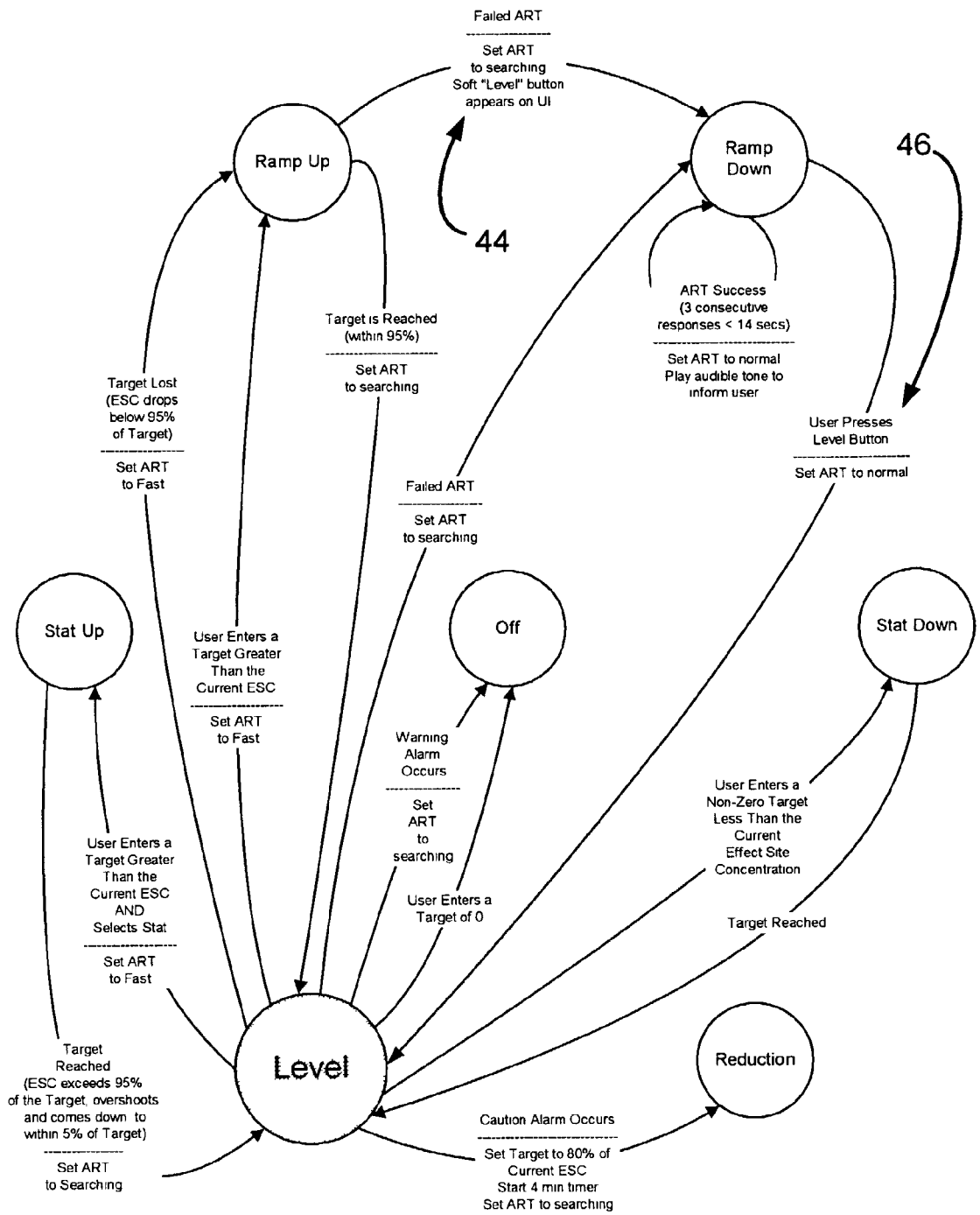
FIG. 13 shows a schematic representation of an alternative drug state model for a LEVEL drug state in accord with embodiments of the present invention.

FIG. 13 shows a graphical chart of transitions to and from an alternative embodiment of the LEVEL drug state that the system may initiate based on certain well-defined events. In a like manner, the other drug states of the present invention may be modified to provide alternative heuristics for achieving their functions. Transitions 44 and 46 are examples of alternative heuristic approaches the drug state model of the present invention may employ.

Figure 12:
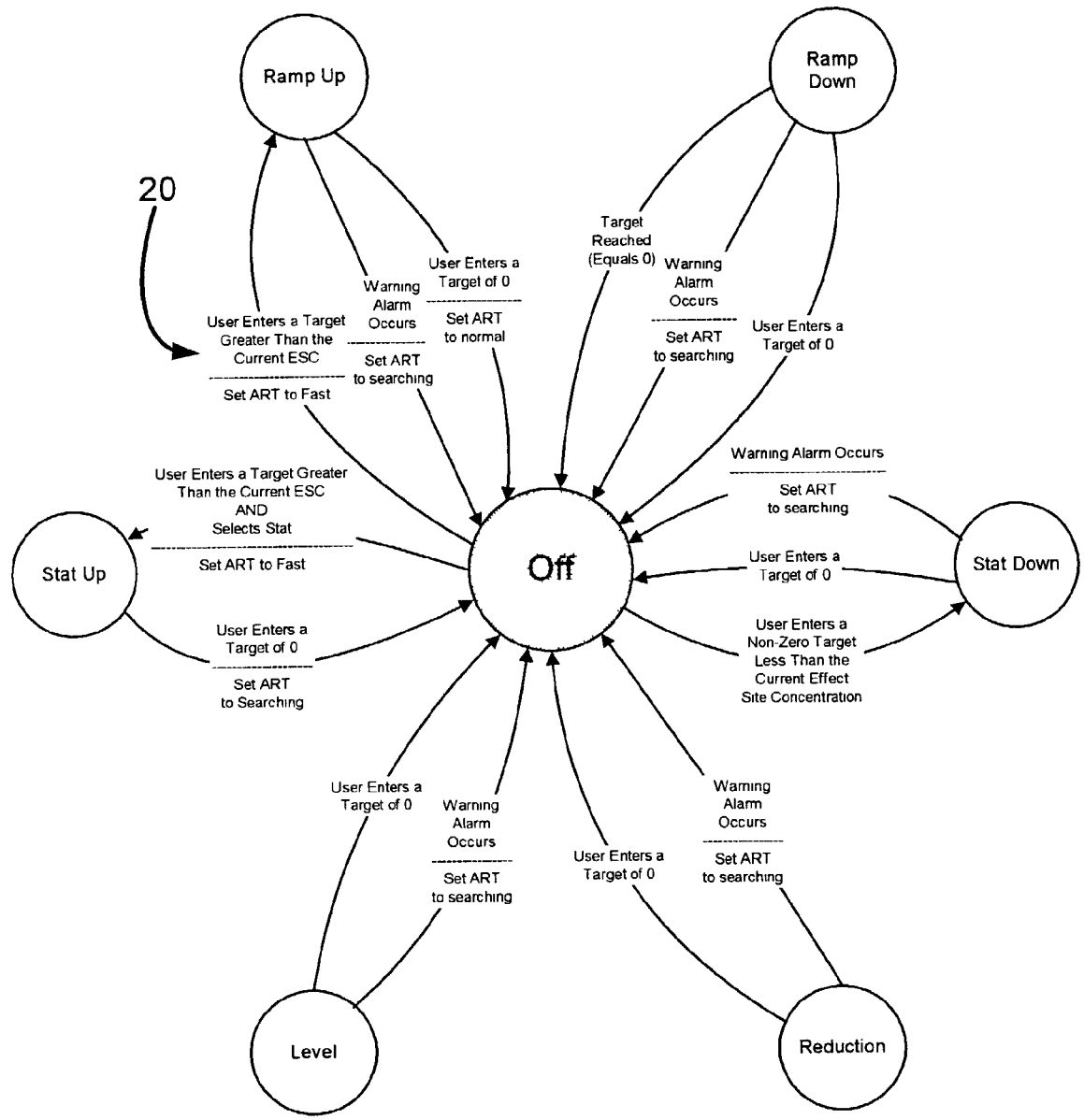
FIG. 12 shows a schematic representation of a drug state model for an OFF drug state in accord with embodiments of the present invention.

FIG. 12 shows a graphical chart of transitions to and from the OFF drug state that the system may initiate based on certain well-defined events. When the system initiates the "OFF" drug state, it immediately and completely discontinues drug administration and ESC may drop, for example, via an exponential decay curve which may be the most rapid possible decrease to zero ESC. The OFF drug state is generally triggered by a Warning alarm, but if users enter a target ESC of zero while in any of the other drug states, the system may transition to the OFF state. The OFF drug state may also be triggered whenever users press a "Stop Propofol" button or the like on the user interface of the system. The ART query cycle frequency may be set to SEARCHING or to NORMAL when the system transitions to OFF.

Table 7a shows possible transitions away from a current drug state of OFF that are possible according to the drug state model of the present invention as based on the occurrence of certain well-defined events. The transitions depicted are those from the current OFF drug state to a new drug state and from the current ART query frequency to a new frequency. Table 7b shows possible transitions to the OFF drug state from the various other drug states and the events that would lead to those transitions according to the drug state model of the present invention.

TABLE 7a

Transitions away from OFF to other drug states

| Event | New drug state | New ART frequency |
|---|---|---|
| User enters target which is > current ESC and selects Stat | STAT UP to target | FAST |
| User enters target which is > current ESC but does not select Stat | RAMP UP to target* | FAST |
| User enters target < current ESC and > 0 | STAT DOWN to target | unchanged |

*Transition 20 (FIG. 12) of the Example run described below

TABLE 7b

Transitions leading to OFF from other drug states

| Previous Drug State | Event |
|---|---|
| STAT UP | User enters new target which = 0 |
| RAMP UP | User enters new target which = 0 |
| RAMP UP | Warning Alarm |
| LEVEL | User enters new target which = 0 |
| LEVEL | Warning Alarm |
| STAT DOWN | User enters new target which = 0 |
| STAT DOWN | Warning Alarm |
| RAMP DOWN | User enters new target which = 0 |
| RAMP DOWN | Warning Alarm |
| RAMP DOWN | Target reached where target was 0 |
| REDUCTION | User enters new target which = 0 |
| REDUCTION | Warning Alarm |

A drug delivery Example Run will now be described in order to illustrate certain embodiments of the drug state transitions that are possible according to the present invention. Each of the particular features of the drug delivery system, the user interface (UI), the automated responsiveness test (ART), and the drug state model that are described in this Example Run are merely exemplary and many alternatives to such features are workable as part of the present invention. Initially, a clinician user enters the patient's demographic data such as, among others, weight, height, age, gender, and ethnicity via a UI of the system. The user then enters a conservative target ESC of propofol by pressing a "Propofol level" button or the like on the UI. At an ensuing prompt, the user presses the button labeled "2.0" and then the "OK" button to actually administer propofol. The drug state model (DSM) then initiates a transition 20 from the OFF state to the RAMP UP drug state (see FIG. 12 and Table 7a above). The rate of infusion in μg/min of propofol is modulated over time by the interface algorithm 40 to achieve a gradual increase in ESC at a constant rate of 0.5 μg/ml/min. This rate is determined by the delivery system according to an algorithm based on the entered demographic data of the patient. During the ramp-up of ESC, the automated responsiveness test (ART) query frequency is set to FAST and queries are initiated every 15 seconds.

In this example, the patient is hypersensitive to propofol and starts to lose responsiveness, as indicated by three consecutive late ART response times to the ART queries, at an ESC of 1.5 μg/ml. The DSM automatically initiates transition 22 from the RAMP UP drug state to the LEVEL drug state (see FIG. 6 and Table 1a above). The DSM sets the ART query frequency to NORMAL. At this point, the procedure starts. Because the system was previously in RAMP UP mode to its user-selected set ESC of 2.0 μg/ml, the ESC concentration slightly overshoots past the ESC of 1.5 μg/ml in effect when the system transitioned to the LEVEL mode. During this temporary overshoot, the patient fails the ART.

The failed ART triggers transition 24 from the LEVEL state to the RAMP DOWN state (see FIG. 11 and Table 6a above). The ESC is then decreased at a constant rate of −0.01 μg/ml/min towards a new target ESC of zero μg/ml. The ART frequency is set to SEARCHING. As the ESC is gradually decreased, the patient regains responsiveness.

Upon the patient's ART "success", the DSM triggers transition 26 from the RAMP DOWN drug state to the LEVEL drug state (see FIG. 7 and Table 2a above). The ART frequency is set to NORMAL. The patient appears to be stable and comfortable. At this point, the patient starts to receive painful stimuli. The clinician user observes that the patient appears to be in pain and her clinical judgment is corroborated by a measured increase in blood pressure and heart rate. The clinician decides to increase the ESC in anticipation of even more painful stimuli yet to come during the procedure.

The clinician enters a higher target ESC by pressing the "Propofol level" button or the like on the UI. At the ensuing prompt, the user presses the button labeled "3.0" to select an ESC of 3.0 μg/ml. Because of the imminence of the very painful stimuli, the user selects Stat delivery by pressing the "Target level stat" button or the like and on the ensuing screen presses "yes" to confirm that she really wants to do this. The DSM initiates transition 28 from the LEVEL state to the STAT UP drug state (see FIG. 8 and Table 3a above) while the ART frequency is set to FAST.

During the "stat-up" drug state, the ESC is increased as fast as possible while allowing no more than, for example, a 15% overshoot past the 3.0 μg/ml target ESC. The patient fails the ART test during the STAT UP ESC increase and the failed ART test is noted on the UI of the medical device to inform the user. However, the DSM does not take any action upon ART failure, consistent with the "clinician knows best" design philosophy of the DSM and keeps on increasing the ESC until the user-selected target is reached. The target is considered to be reached when the ESC first enters within 5% of the 3.0 μg/ml target (i.e., $2.85 \leq ESC \leq 3.15$). Upon the target being reached, the DSM initiates transition 29 from STAT UP to the LEVEL drug state while the ART frequency is set to searching (see FIG. 8 and Table 3a above). In the LEVEL drug state, the ESC is maintained at the 3.0 μg/ml target ESC with an accuracy of ±5%. In the subsequent vigorous stimulation of the patient caused by the procedure, ART success occurs thereby vindicating the user's experience that the painful stimulus may counter the deeper sedation. The ART success triggers the system to change the ART frequency from FAST to NORMAL.

Once the most painful part of the procedure is over and as the painful stimuli become less intense, the patient starts to have late ART responses but the DSM takes no action. The clinician resets the target ESC to a lower value of 2.0 µg/ml in anticipation that the ESC of 3.0 µg/ml may be too high now that the stimuli are not as painful. To do so, the clinician presses the "Propofol level" button on the UI. At the ensuing screen, the user presses the button labeled "2.0" to select an ESC of 2.0 µg/ml followed by the "yes" button to confirm that she really wants to do this. The DSM initiates transition 30 from LEVEL to the STAT DOWN drug state (see FIG. 9 and Table 4a above) while the ART frequency is left unchanged from its setting prior to the transition, i.e., NORMAL. During the STAT DOWN drug state, the drug infusion rate is set to zero initially to reach the lower ESC set point as fast as possible. Subsequently, when the ESC first reaches the 2.0 µg/ml target ±5% (i.e., $1.9 \leq ESC \leq 2.1$), the DSM initiates transition 32 from STAT DOWN to the LEVEL drug state (see FIG. 9 and Table 4a above). The ESC is maintained within ±5% of the 2.0 µg/ml target while the ART frequency remains unchanged at NORMAL.

As the procedure begins to wind down, the clinician becomes slightly concerned about the slow heart rate of the patient and decides to administer some atropine. Distracted by her pager going off, she instead grabs a syringe containing fentanyl, a respiratory depressant, and injects it, without realizing her mistake. The patient's breathing rate starts to slow down and a capnometer detects the decrease in respiratory rate and triggers a caution alarm when the breathing rate falls below the caution alarm level.

The caution alarm generates an audible and visual alarm on the medical device to alert the user while the DSM initiates transition 34 from the LEVEL drug state to the REDUCTION drug state (see FIG. 10 and Table 5a above). The audible alarm helps the user to realize her mistake and she immediately administers naloxone (Narcan) to reverse the effect of the inadvertent fentanyl. As a result of entering the REDUCTION drug state, the target ESC is set to 80% of the current 2.0 µg/ml ESC (i.e., to 1.6 µg/ml), a 4-minute timer is started, and the ART frequency is set to searching.

Before the 4-minute timer elapses, the procedure is over. The user then presses the "Stop propofol" button on the UI. This action is equivalent to setting the target ESC to zero µg/ml thereby causing a transition 36 from the REDUCTION drug state to the OFF drug state (see FIG. 10 and Table 5a above).

The drug delivery system of this invention may also have a recognition function integrated into the software algorithms for controlling the rate of drug administration to assure that certified drugs (i.e. known concentration and purity) and supplies (i.e. known calibration and quality) are utilized as a part of the system. This recognition system "reads" the identification of the drug or supply that is attached to the system for use therewith. If a non-certified drug or supply is attached, the system will not initiate the administration of sedative or analgesic drugs. Additionally, in related alternative embodiments, it is also feasible and desirable to package these items along with other supplies in a kit that has integrated into it the ability to be recognized and "read" by the system as quality certified. The system may also have a writing function integrated into the software algorithms in order to avoid re-use and/or contamination problems. The writing function has the ability to "write" to a tagged supply article that it has been contaminated through use and "label" or "code" it appropriately. For multiple use articles susceptible to contamination, the system can provide a "rewrite" function, enabling the article to only be used again after it has been properly cleaned and quality certified for re-use. Further, it is possible for the write function to store information regarding the number of cycles of use that the article has experienced and to compare this information to the certified life cycle limit. An alarm can sound when the limit is being approached and, once the limit is met, the invention will not recognize the device until it is replaced. Such tagging and verification can be accomplished through various means, including through electronic and physical tags such as are disclosed in U.S. patent application Ser. No. 10/151,255 filed May 21, 2002 and application Ser. No. 60/324,043, filed Sep. 24, 2001, the entirety of each of which are herein incorporated by reference.

We claim:

1. A system for providing drug delivery to a patient, wherein said system comprises:
    a user interface for accepting input from a user;
    a drug delivery device that delivers an amount of drug to a patient;
    two or more patient health monitors adapted so as to be coupled to a patient and generate a signal reflecting at least one health condition of the patient; and
    a processor that integrates the user interface, drug delivery device, and patient health monitors according to a hierarchy of software algorithms defining different drug states that seamlessly allow for drug level adjustments by the user such that the amount of drug delivered to the patient by the delivery device is modulated based on an input from the user and based on a signal generated by the patient health monitors to achieve a target effect site concentration (ESC),
    wherein said hierarchy of software algorithms include a drug state model and a flow control algorithm and an interface algorithm, said interface algorithm being one of a rate controlled infusion algorithm and a target controlled infusion algorithm that run in real time and said interface algorithm being capable of producing different time profiles of a target drug concentration at different effect sites, and
    wherein automated actions initiated by said processor will not increase overall drug levels automatically without an explicit request for a higher drug level by said user.

2. The system for providing drug delivery of claim 1, wherein one of said two or more patient health monitors is an automated responsiveness test monitor.

3. The system for providing drug delivery of claim 2, wherein said drug state model includes the following states: RAMP UP; RAMP DOWN; LEVEL; and OFF.

4. The system for providing drug delivery of claim 3, wherein said drug state model further comprises the following states: STAT UP; STAT DOWN; and REDUCTION.

5. The system for providing drug delivery of claim 3, wherein said RAMP UP state is the default state whenever said user enters a new target ESC which is greater than the current ESC.

6. The system for providing drug delivery of claim 3, wherein said RAMP DOWN state is the default state whenever said user enters a new target ESC which is less than the current ESC.

7. The system for providing drug delivery of claim 1, wherein said interface algorithm employs a pre-programmed infusion rate template.

8. The system for providing drug delivery of claim 1, wherein said drug is at least one of a sedative, amnestic and analgesic drug.

9. The system for providing drug delivery of claim 1, wherein monitoring sites for said patient health monitors include at least one of said patient's blood plasma, brain, central nervous system, neuromuscular junction, alveolar space, kidney, liver, pancreas, hypothalamus, heart tissue and baroreceptors.

10. The system for providing drug delivery of claim 1, wherein said flow control algorithm manages said delivery controller so that the drug is accurately delivered at a requested infusion rate.

11. The system of claim 1, wherein at least one of said two or more patient health monitors is an electroencephalogram (EEG) used to assess the patient's consciousness.

12. The system of claim 1, wherein said processor incorporates additional user input to override automated functions without switching operating modes.

13. A method for providing drug delivery to a patient, wherein said method comprises the steps of:
accepting input from a user via a user interface;
delivering an amount of drug to a patient via a drug delivery device;
generating a signal reflecting at least one health condition of the patient via two or more patient health monitors adapted so as to be coupled to a patient; and
integrating the user interface, drug delivery device, and patient health monitors according to a hierarchy of software algorithms defining different drug states that account for the event of additional input from the user using a clinician-knows-best logic such that the amount of drug delivered to the patient by the delivery device is modulated based on an input from the user and based on a signal generated by the patient health monitors to achieve a target ESC;
wherein said hierarchy of software algorithms include a drug state model and a flow control algorithm and an interface algorithm, said interface algorithm being one of a rate controlled infusion algorithm and a target controlled infusion algorithm that run in real time and are capable of producing different time profiles of a target drug concentration at different effect sites, and
wherein said hierarchy of algorithms will not result in an increase in overall drug levels to said patient without an explicit request for a higher drug level by said user.

14. The method for providing drug delivery of claim 13, wherein one of said two or more patient health monitors is an automated responsiveness test monitor.

15. The method for providing drug delivery of claim 14, wherein said drug state model is a finite state algorithm.

16. The method for providing drug delivery of claim 15, wherein said drug state model includes the following states: RAMP UP; RAMP DOWN; LEVEL; and OFF.

17. The method for providing drug delivery of claim 16, wherein said drug state model further comprises the following states: STAT UP; STAT DOWN; and REDUCTION.

18. The method for providing drug delivery of claim 16, wherein said RAMP UP state is the default state whenever said user enters a new target ESC which is greater than the current ESC.

19. The method for providing drug delivery of claim 16, wherein said RAMP DOWN state is the default state whenever said user enters a new target ESC which is less than the current ESC.

20. The method for providing drug delivery of claim 13, wherein said interface algorithm employs a pre-programmed infusion rate template.

21. The system for providing drug delivery of claim 13, wherein said drug is at least one of a sedative, amnestic and analgesic drug.

22. The method for providing drug delivery of claim 13, wherein monitoring sites for said patient health monitors include at least one of said patient's blood plasma, brain, central nervous system, neuromuscular junction, alveolar space, kidney, liver, pancreas, hypothalamus, heart tissue and baroreceptors.

23. The method for providing drug delivery of claim 13, wherein said flow control algorithm manages said delivery controller so that the drug is accurately delivered at a requested infusion rate.

24. The method of claim 13, wherein said signal reflecting at least one health condition of the patient is an EEG signal to assess the patient's consciousness.

25. A system for providing computer-assisted drug delivery, wherein said system comprises:
a user interface for accepting input from a user;
a drug delivery device that delivers an amount of drug to a patient, wherein said drug is at least one of a sedative, amnestic and analgesic drug;
two or more patient health monitors adapted so as to be coupled to a patient and generate a signal reflecting at least one health condition of the patient, wherein one of said two or more patient health monitors is an automated responsiveness test; and
a processor that integrates the user interface, drug delivery device, and patient health monitors according to a hierarchy of software algorithms defining different drug states that account for the event of drug level adjustments by the user such that the amount of drug delivered to the patient by the delivery device is modulated based on an initial input from the user and based on a signal generated by the patient health monitors without further user input, if the automated action will maintain or decrease a drug level, and automatically altering said drug states to incorporate said drug level adjustments by the user; wherein said system determines a drug level limit based on automated responsiveness test data received during a gradual drug increase initiated by the user, and wherein said drug level limit does not exceed the initial user input level, and wherein said automated responsiveness test query cycle frequency is set to FAST during said gradual drug increase.

26. The system of claim 25, wherein said two or more patient health monitors further comprise at least one of a pulse oximeter and non-invasive blood pressure monitor.

27. The system of claim 26, wherein said two or more patient health monitors further comprise at least one of a capnometer and ECG.

28. The system of claim 25, wherein a warning alarm indicates one or more failed response to said automated responsiveness test during a linear drug increase initiated by the user.

29. The system of claim 28, wherein said automated responsiveness test query cycle frequency is set to FAST during said linear drug increase.

30. The system of claim 25, wherein said system decreases a drug infusion rate upon receiving one or more failed responses to said automated responsiveness test.

31. The system of claim 30, wherein system maintains said drug infusion rate upon receiving one or more successful responses to said automated responsiveness test during said decrease of drug infusion rate.

32. The system of claim 25, wherein said system will prevent initiation of drug delivery if said signal reflecting at least one health condition of the patient is below acceptable values.

33. The system of claim 25, wherein at least one of said two or more patient health monitors is an electroencephalogram (EEG) used to assess the patient's consciousness.

* * * * *